United States Patent
Kim et al.

(10) Patent No.: US 10,544,190 B2
(45) Date of Patent: Jan. 28, 2020

(54) PEPTIDE THAT SUPRESSES BINDING OF BETA-AMYLOID AND RAGE

(71) Applicant: ENSOL BIOSCIENCES INC., Daejeon (KR)

(72) Inventors: Hae Jin Kim, Daejeon (KR); Eun Joung Moon, Gyeongsan-si (KR); Duk Soon Hwang, Daejeon (KR)

(73) Assignee: ENSOL BIOSCIENCES INC., Daejeon (KR)

( * ) Notice: Subject to any disclaimer, the term of this patent is extended or adjusted under 35 U.S.C. 154(b) by 0 days.

(21) Appl. No.: 16/309,557

(22) PCT Filed: Mar. 24, 2017

(86) PCT No.: PCT/KR2017/003214
§ 371 (c)(1),
(2) Date: Dec. 13, 2018

(87) PCT Pub. No.: WO2018/016714
PCT Pub. Date: Jan. 25, 2018

(65) Prior Publication Data
US 2019/0161517 A1    May 30, 2019

(30) Foreign Application Priority Data
Jul. 20, 2016  (KR) .......................... 10-2016-0091824

(51) Int. Cl.
*C07K 7/06* (2006.01)
*A61P 25/28* (2006.01)
*A61K 38/00* (2006.01)

(52) U.S. Cl.
CPC ................. *C07K 7/06* (2013.01); *A61P 25/28* (2018.01); *A61K 38/00* (2013.01)

(58) Field of Classification Search
CPC .......... A61K 38/00; A61K 38/08; A61P 25/28; C07K 7/06
See application file for complete search history.

(56) References Cited

U.S. PATENT DOCUMENTS 4,895,841 A    1/1990 Sugimoto et al.

FOREIGN PATENT DOCUMENTS

| JP | 2009-524680 A | 7/2009 |
| KR | 10-2011-0136504 A | 12/2011 |
| KR | 10-1215821 B1 | 12/2012 |
| KR | 10-2013-0090144 A | 8/2013 |
| KR | 10-1595630 B1 | 2/2016 |
| WO | 2006-031330 A2 | 3/2006 |

OTHER PUBLICATIONS

Vickers. A vaccine against Alzheimer's disease: developments to date. Drugs Aging 2002; 19(7):487-94.*
Perrin et al. Multimodal techniques for diagnosis and prognosis of Alzheimer's disease. Nature Oct. 15, 2009;461(7266):916-22, Published online Oct. 14, 2009.*
Hampel et al. The future of Alzheimer's disease: the next 10 years. Prog Neurobiol. Dec. 2011;95(4):718-28. Epub Nov. 22, 2011.*
Bert H.-O. Gutler et al., "A quantitative analysis of spontaneous isoaspartate formation from N-terminal asparaginyl and aspartyl residues", Amino Acids, Jan. 24, 2013, pp. 1205-1214, vol. 44.
G. Brent Irvine, Omar M El-Agnaf, Ganesh M Shankar, Dominic M Walsh, Protein aggregation in the brain: the molecular basis for Alzheimer's and Parkinson's diseases, Mol Med, Jul.-Aug. 2008, pp. 451-464, vol. 14.
Rashid Deane, Benjamin L. Miller, Berislav V, Zlokovi, A multimodal RAGE-specific inhibitor reduces amyloid B-mediated brain disorder in a mouse model of Alzheimer disease, The Journal of Clinical Investigation, Apr. 2012, pp. 1377-1392, vol. 122.
Holly Oakley et al., Intraneuronal B-Amyloid Aggregates, Neurodegeneration, and Neuron Loss in Transgenic Mice with Five Familial Alzheimer's Disease Mutations: Potential Factors in Amyloid Plaque Formaton, The Journal of Neuroscience, Oct. 4, 2006, pp. 10129-10140, vol. 22.
P. Tiraboschi, L.A. Hansen, L.J. Thal, J. Corey-Bloom, The importance of neuritic plaques and tangles to the development and evolution of AD, Neurology, Jun. 7, 2004, pp. 1984-1989, vol. 62.

* cited by examiner

*Primary Examiner* — Gregory S Emch
(74) *Attorney, Agent, or Firm* — Novick, Kim & Lee, PLLC; Jae Youn Kim

(57) ABSTRACT

The present invention provides a peptide consisting of the amino acid sequence of SEQ ID NO:1 or the amino acid sequence of SEQ ID NO:2, or a pharmaceutically acceptable salt thereof and a use thereof. The present invention can inhibit the entry of beta-amyloid into the brain. In addition, the present invention can be applied more easily with respect to the suppression of the intracerebral action of beta-amyloid and thus is advantageous in having excellent applicability.

5 Claims, 3 Drawing Sheets
Specification includes a Sequence Listing.

PEPTIDE THAT SUPRESSES BINDING OF BETA-AMYLOID AND RAGE

INCORPORATION OF SEQUENCE LISTING

This application contains a sequence listing submitted in Computer Readable Form (CRF). The CFR file containing the sequence listing is entitled "9-PK002172917-Sequence-Listing.txt", which was created and modified on Dec. 12, 2018, and is 900 bytes in size. The information in the sequence listing is incorporated herein by reference in its entirety.

TECHNICAL FIELD

The present invention relates to a novel peptide, and more particularly to a novel peptide exhibiting an effect of inhibiting the entry of beta-amyloid into the brain and the use thereof.

BACKGROUND ART

Beta-amyloid, which acts in the brain, is known to cause diseases, including Alzheimer's disease, dementia such as vascular dementia, alcoholic dementia and dementia with Lewy bodies, Parkinson's disease, Huntington's disease, and inflammation of the brain (Irvine G B, El-Agnaf O M, Shankar G M, Walsh D M. "Protein aggregation in the brain: the molecular basis for Alzheimer's and Parkinson's diseases" Mol Med. 2008; 14(7-8):451-64, etc.). In particular, Alzheimer's disease (AD) is the most common degenerative brain disease that causes dementia, accounting for 55-70% of all dementia.

Most of the drugs currently developed for dementia are acetylcholinesterase inhibitors that inhibit the degradation of acetylcholine, which is a neurotransmitter that is very important for memory function (U.S. Pat. No. 4,895,841, etc.). The acetylcholinesterase inhibitors focus on symptom relief rather than eliminating the cause thereof. Major side effects of these drugs include hyperactivity of the parasympathetic nervous system owing to excessive increase of acetylcholine, resulting in adverse digestive and neuropsychiatric events such as severe diarrhea, nausea, vomiting, depression, anxiety, insomnia, headaches, and the like. These drugs are difficult to use as practical therapeutic agents for Alzheimer's disease.

Meanwhile, peptides comprising the specific amino acid sequence (DAEF) are known as neuroprotective peptides that inhibit beta-amyloid-induced neuronal cytotoxicity (International Patent Publication No. WO 2006/031330 A2). Such peptides are known only to reduce or prevent beta-amyloid-induced effects such as tau protein phosphorylation or neuronal cell death.

Furthermore, since such a neuroprotective peptide needs to pass through a blood-brain barrier (BBB) in order to exhibit effects in the brain, additional means for entry into the brain (e.g., a catheter inserted by neurosurgery, etc.) has to be applied, which is considered difficult.

Accordingly, there is a need to develop drugs that may be more easily applied with the goal of inhibiting the intracerebral action of beta-amyloid.

CITATION LIST

Patent Literature (Patent Document 1) U.S. Pat. No. 4,895,841, Jan. 23, 1990, Abstract (Patent Document 2) International Patent Publication No. WO 2006/031330 A2, Mar. 23, 2006,

Non-Patent Literature (Non-Patent Document 1) Irvine G B, El-Agnaf O M, Shankar G M, Walsh D M. "Protein aggregation in the brain: the molecular basis for Alzheimer's and Parkinson's diseases" Mol Med. 2008; 14(7-8):451-64

DISCLOSURE OF INVENTION

Technical Problem

The technical problem to be solved by the present invention is to provide a novel peptide having high applicability.

In addition, the other technical problem to be solved by the present invention is to provide the use of the peptide of the present invention.

The technical problems to be solved by the present invention are not limited to the foregoing, and additional technical problems, which are not mentioned herein, will be readily understood by those skilled in the art from the following description.

Solution to Problem

The present invention provides a peptide consisting of the amino acid sequence of SEQ ID NO:1 (DGEFF) or the amino acid sequence of SEQ ID NO:2 (DGEF), or a pharmaceutically acceptable salt thereof.

In the amino acid sequence, D designates aspartic acid (Asp), G designates glycine (Gly), E designates glutamic acid (Glu), and F designates phenylalanine (Phe).

The amino acids that constitute the peptide include L-, D-, and DL-forms, all of which are incorporated in the amino acids of the peptide of the present invention. Also, it will be apparent that D may be interpreted as having a meaning including aspartic acid, as well as aspartate, as the amino acid. Furthermore, it will be apparent that E may be interpreted as having a meaning including glutamic acid, as well as glutamate, as the amino acid.

The peptide includes variants thereof in which a portion of the peptide structure according to the present invention is varied by natural mutation or artificial mutation without changing the main activity thereof.

Examples of the pharmaceutically acceptable salt may include hydrochloride, sulfate, phosphate, acetate, citrate, tartrate, succinate, lactate, maleate, fumarate, oxalate, methane sulfonate, and para-toluene sulfonate.

Both the amino acid sequence of SEQ ID NO:1 (DGEFF) and the amino acid sequence of SEQ ID NO:2 (DGEF) include DGEF in common. The present inventors have ascertained that the peptide or pharmaceutically acceptable salt thereof according to the present invention, having the common sequence, is effective at inhibiting the entry of beta-amyloid into the brain through the following tests.

Thereby, the present invention is capable of more directly and easily inhibiting the intracerebral action (intracerebral deposition, etc.) of beta-amyloid. Specifically, the present invention is capable of easily inhibiting the intracerebral action of beta-amyloid even without the application of additional means (e.g. a catheter inserted by neurosurgery, etc.) for passing through a blood-brain barrier. Also, the present invention is capable of inhibiting the entry of beta-amyloid alone into the brain, thus exhibiting more direct effects on beta-amyloid-related diseases, symptoms and the like. This is because the treatment, prevention and alleviation of diseases and symptoms caused by intracerebral action of beta-amyloid may become possible by suppressing the intracerebral action of beta-amyloid due to inhibition of entry of beta-amyloid into the brain.

The inhibition of entry of beta-amyloid into the brain may result from suppressing the binding of beta-amyloid and RAGE (Receptor for Advanced Glycation End products) using the peptide or pharmaceutically acceptable salt thereof according to the present invention. RAGE is a receptor for transporting beta-amyloid into the brain, and the peptide or pharmaceutically acceptable salt thereof according to the present invention binds to RAGE in place of beta-amyloid, thereby suppressing the binding of beta-amyloid to RAGE, whereby the entry of beta-amyloid into the brain may be inhibited.

Therefore, the present invention provides the use of the peptide or pharmaceutically acceptable salt thereof according to the present invention, and preferably the use thereof for inhibition of entry of beta-amyloid into the brain or for the treatment or prevention of at least one selected from among Alzheimer's disease, dementia, Parkinson's disease, Huntington's disease, and inflammation of the brain. Here, the term "treatment" comprehensively means the reduction or alleviation of symptoms, and the term "prevention" is used with a comprehensive meaning including inhibition of progression of the disease from the asymptomatic stage before disease. The dementia may be at least one selected from among Alzheimer's dementia, vascular dementia, alcoholic dementia, and dementia with Lewy bodies.

At least one selected from among Alzheimer's disease, dementia, Parkinson's disease, Huntington's disease, and inflammation of the brain may be caused by the deposition of beta-amyloid in the brain.

The treatment or prevention may be due to inhibition of entry of beta-amyloid into the brain.

Also, the treatment or prevention may be due to at least one selected from among inhibition of deposition of beta-amyloid in the brain and inhibition of inflammation of the brain.

The inhibition of deposition of beta-amyloid may result from the inhibition of entry of beta-amyloid into the brain.

Therefore, the present invention provides an inhibitor for the inhibition of entry of beta-amyloid into the brain, comprising the peptide or pharmaceutically acceptable salt thereof according to the present invention.

Also, the present invention provides a composition for the treatment or prevention of at least one selected from among Alzheimer's disease, dementia, Parkinson's disease, Huntington's disease, and inflammation of the brain, comprising the peptide or pharmaceutically acceptable salt thereof according to the present invention. The composition may be a pharmaceutical composition.

The inhibitor or the composition may contain, as an active ingredient, the peptide or pharmaceutically acceptable salt thereof according to the present invention.

The inhibitor or the composition further contains a pharmaceutically acceptable additive, and may be composed of the peptide or pharmaceutically acceptable salt thereof according to the present invention and the additive as above.

The peptide of the present invention may be prepared by methods typically useful in the field of peptide chemistry. For example, the peptide may be prepared by the method disclosed by Schroder and Lubke, ⌈The Peptides⌉ vol. 1, Academic Press, New York (1965), or by the method such as solution synthesis or solid synthesis.

Examples of the process for forming a peptide bond may include an acyl azide method, an acyl halide method, an acyl imidazole method, a carbodiimide method, a phosphonium method, an anhydride method, a mixed anhydride method, an oxidation-reduction method, and the use of Woodward regent K.

Before the condensation reaction, a carboxyl group, an amino group or the like, not participating in the reaction, may be protected, and a carboxyl group that participates in the condensation reaction may be activated by methods known in the art.

Examples of the functional group for protecting the carboxyl group may include ester-forming groups, such as methyl, tert-butyl, aryl, pentafluorophenyl, benzyl, paramethoxybenzyl, and methoxyethoxymethyl.

Examples of the functional group for protecting the amino group may include trityl carbonyl, aryloxycarbonyl, cyclohexyloxycarbonyl, trichloroethyloxycarbonyl, benzyloxycarbonyl, tert-butoxycarbonyl, and/or 9-fluorenylmethyloxycarbonyl.

Examples of the active form of the carboxyl group may include mixed anhydride, azide, acyl chloride, and active ester [ester with alcohol (e.g. pentachlorophenol, 2,4-dinitrophenol, cyanomethyl alcohol, p-nitrophenol, N-hydroxy-5-norborene-2,3-dicarboxylimide, N-hydroxysuccinimide, N-hydroxyphthalimide, or 1-hydroxybenzotriazole)].

The solvent usable in the condensation reaction for forming a peptide bond may include benzene, toluene, hexane, acetone, nitromethane, cyclohexane, ether, chloroform, dichloromethane, ethyl acetate, N,N-dimethylformamide, dimethylsulfoxide, pyridine, dioxane, tetrahydrofuran, water, methanol, and ethanol, which may be used alone or in combination.

The reaction temperature may range from about $-70°$ C. to $100°$ C., which is typically applied in a reaction, and preferably from $-30°$ C. to $30°$ C.

The deprotection reaction for removing the protecting group from the peptide may be carried out using an acid compound, a base compound, or a transition metal, capable of removing the protecting group without influencing the peptide bond, depending on the kind of protecting group.

The deprotection reaction may be performed through acid treatment using, for example, hydrogen chloride, hydrogen bromide, hydrogen fluoride, acetic acid, methanesulfonic acid, trifluoromethanesulfonic acid, trifluoroacetic acid, trimethylchlorosilane, or mixtures thereof.

When the deprotection reaction is carried out through acid treatment, it may be promoted by the addition of an adjuvant such as anisole, phenol or thioanisole.

Alternatively, the deprotection reaction may be performed through base treatment using, for example, ammonia, diethylamine, hydrazine, morpholine, N-methylpyrrolidine, piperidine, sodium carbonate, or mixtures thereof.

Alternatively, the deprotection reaction may be performed through transition metal treatment using, for example, zinc, mercury, palladium/hydrogen, etc.

After completion of the reaction, the peptide may be purified using a typical peptide purification process, such as extraction, layer separation, solid precipitation, recrystallization, or column chromatography.

Moreover, the peptide according to the present invention may be converted into a variant thereof or a pharmaceutically acceptable salt thereof using a typical process.

The peptide according to the present invention may be synthesized using an automatic peptide synthesizer, or may be produced through genetic manipulation. For example, a fusion gene encoding a fusion protein consisting of a fusion partner and the peptide according to the present invention is manufactured through genetic manipulation, and is then used to transform a host microorganism, and the fusion protein is expressed in the host microorganism, after which the peptide according to the present invention is cleaved or separated from the fusion protein using a protease or compound, thus yielding a desired peptide.

The peptide or pharmaceutically acceptable salt thereof according to the present invention is parenterally administered in an amount of 200 mg/day to 500 mg/day, and preferably 267 mg/day to 400 mg/day. Upon oral administration, the amount thereof corresponds to 2 to 5 times the amount upon parenteral administration. The administration may be conducted once a day or several times a day, and the amount thereof may be based on an adult (weighing 60 kg), but may vary depending on the weight, body condition, and the like. The peptide or pharmaceutically acceptable salt thereof according to the present invention may be mainly administered through parenteral routes, for example, topical injection, intravenous or subcutaneous injection, intracerebroventricular or intraspinal administration, transdermal administration, or intranasal or intrarectal administration. In some cases, oral administration is possible.

The peptide or pharmaceutically acceptable salt thereof, the inhibitor or the composition according to the present invention may be formulated in the form of an injection, a suppository, a powder, a nose drop, a granule, a tablet, or a transdermal patch, together with a pharmaceutically acceptable additive.

The pharmaceutically acceptable additive may be applied depending on a variety of factors well known to those skilled in the art, including, for example, a specific bioactive material, its concentration, stability and intended bioavailability; disorders and diseases to be treated or conditions associated therewith; individuals to be treated, their age, size, and general health status; and composition administration routes, for example, nasal, oral, ocular, topical, dermal and muscular routes, but the present invention is not limited thereto. The pharmaceutically acceptable additive, which is used for administration of the bioactive material, in addition to the oral administration route, may include an aqueous solution including D5W (5% glucose in water), dextrose and a physiological salt in an amount within 5% of the volume thereof. For topical intralesional injection, any injectable hydrogel may be used to enhance the therapeutic effects and increase the duration thereof. The pharmaceutically acceptable additive may contain additional components for improving the stability of active components such as preservatives and antioxidants.

The peptide or pharmaceutically acceptable salt thereof, the inhibitor, or the composition according to the present invention may be formulated through appropriate methods in the related field, and for example, is preferably formulated so as to be suitable for each disease or component in accordance with the methods disclosed in Remington's Pharmaceutical Science, Mack Publishing Company, Easton Pa. (latest).

The peptide of the present invention may be stored in a saline solution, or may be lyophilized in an ampoule after the addition of mannitol or sorbitol and may be administered after dissolution in saline.

In addition, the present invention provides a method of inhibiting the entry of beta-amyloid into the brain, comprising administering the peptide or pharmaceutically acceptable salt thereof according to the present invention to a mammal, including a human, in need of administration. In addition, the present invention provides a method of treating or preventing at least one selected from among Alzheimer's disease, dementia, Parkinson's disease, Huntington's disease, and inflammation of the brain, comprising administering the peptide or pharmaceutically acceptable salt thereof according to the present invention to a mammal, including a human, in need of administration. In addition, the present invention provides the use of the peptide or pharmaceutically acceptable salt thereof according to the present invention in the manufacture of an inhibitor for inhibiting the entry of beta-amyloid into the brain. In addition, the present invention provides the use of the peptide or pharmaceutically acceptable salt thereof according to the present invention in the manufacture of a medicament for the treatment or prevention of at least one selected from among Alzheimer's disease, dementia, Parkinson's disease, Huntington's disease, and inflammation of the brain. The administered peptide or pharmaceutically acceptable salt thereof may be a peptide or pharmaceutically acceptable salt thereof in an effective amount.

Unless otherwise mentioned, the matters described in connection with the peptide or pharmaceutically acceptable salt thereof, the use, the inhibitor, the composition, and the method according to the present invention are applied equally to each other in the same scope unless they are contradictory to each other.

Advantageous Effects of Invention

The present invention is effective at inhibiting the entry of beta-amyloid into the brain. Also, the present invention can be more easily applied in association with inhibition of the intracerebral action of beta-amyloid, thus exhibiting high applicability.

MODE FOR THE INVENTION

Figure 1:
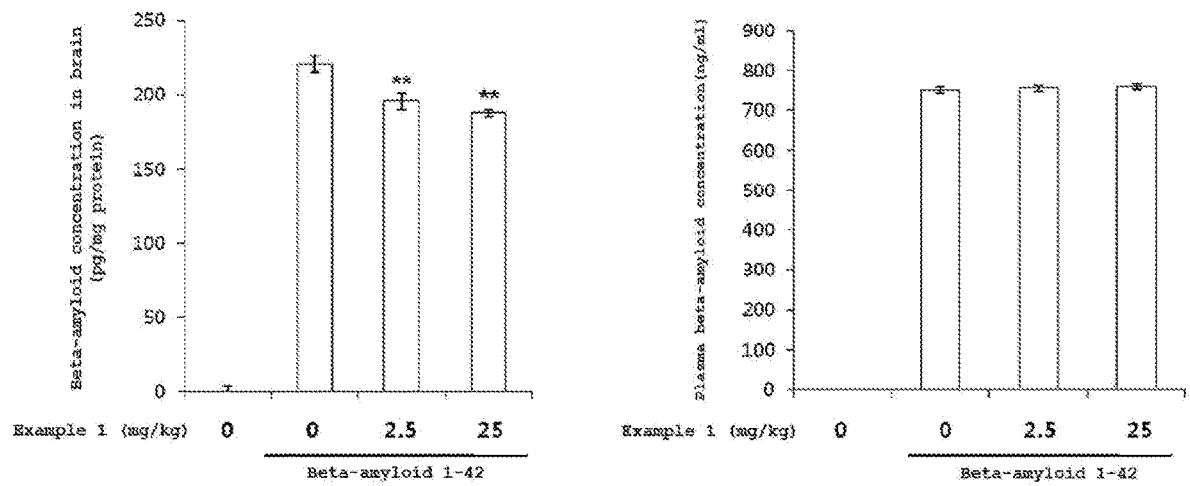
FIG. 1 is graphs showing the results of evaluation of the effect of inhibiting the entry of blood beta-amyloid into the brain according to an embodiment of the present invention.

A peptide or a pharmaceutically acceptable salt thereof according to the present invention is not known. International Patent Publication No. WO2006/031330 A2 discloses beta-amyloid-related peptides, but all of these peptides are associated with the reduction or prevention of effects induced by the action of beta-amyloid alone, particularly the effects of inhibiting beta-amyloid-induced tau protein phosphorylation or neuronal cell death, and thus are known only as neuroprotective peptides. These neuroprotective peptides are known to inhibit beta-amyloid-induced effects such as neuronal cell death and tau phosphorylation. The effects of the neuroprotective peptides are different from the effect of inhibiting the entry of beta-amyloid into the brain according to the present invention. The present invention has an effect of inhibiting the entry of beta-amyloid into the brain and may thus exhibit high applicability because of the application without the need to pass through a blood-brain barrier (BBB), whereas the neuroprotective peptide has to pass through a blood-brain barrier (BBB) in order to exhibit intracerebral activity thereof. Ultimately, the neuroprotective peptide requires additional means for entry into the brain (e.g., a catheter inserted by neurosurgery, etc.) for the desired activity, but the present invention also has an unexpected effect from the neuroprotective peptide in that it requires no additional means for entry into the brain. Thus, the effect of the present invention is not only completely different from, but also unpredictable from, the effects of the peptides disclosed in International Publication No. WO 2006/031330 A2. Furthermore, as shown in the following test results, the neuroprotective peptides do not exhibit the effect of inhibiting entry of beta-amyloid into the brain, and thus it can be reconfirmed that the present invention is not only completely different from such peptides, but also has an unpredictable effect.

A better understanding of the present invention is given through the following examples, comparative examples and preparation examples, wherein the examples and preparation examples are merely set forth to illustrate the present invention but are not to be construed as limiting the present invention.

The reagents used in the following examples and the like are commercially available and best products, and are purchased from Sigma-Aldrich, unless otherwise mentioned. For the following test results, means and standard deviations were measured and statistical significance was assayed, as necessary.

<Preparation of Peptide>

The peptides shown in Table 1 below were prepared by AnyGen Co., Ltd., Korea. Specifically, these peptides were synthesized by a solid-phase method using the chemical properties of Fmoc (9-fluorenyl-methoxycarbonyl). More specifically, a C-terminus of the peptide was bound to 0.55 mmol/g of a solid-phase resin (Wang resin; Sigma-Aldrich). The coupling of Fmoc-Phe-OH amino acid was carried out together with O-Benzotriazole-N,N,N',N'-tetramethyl-uronium-hexafluoro-phosphate (HBTU). The amino acid side-chain was protected by tert-butyl and tert-butyloxycarbonyl. Deprotection and separation from the resin were performed at room temperature for 3 hr using a mixed solution comprising trifluoroacetic acid and water at a ratio of 95:5 (v/v). A crude peptide was repeatedly washed with diethylether, dried in a vacuum, and then purified via reverse-phase high-performance liquid chromatography (RP-HPLC) using a Shimadzu 8 μm Shimpak ODS C18 column (20×250 mm). The purified peptide was identified via analytical RP-HPLC using a Shimpak 5 μm ODS C18 column (4.6×250 mm). The molecular weight of the synthesized peptide was measured using a matrix-assisted laser desorption ionization (MALDI)-mass spectrometer (Axima CFR, Kratos Analytical, Manchester, UK).

TABLE 1

| | Amino acid sequence | SEQ ID NO: |
|---|---|---|
| Example 1 | DGEFF | 1 |
| Example 2 | DGEF | 2 |
| Comparative Example 1 | DAEF | 3 |
| Comparative Example 2 | VKMDAEFR | 4 |

In Table 1, D designates aspartic acid (Asp), G designates glycine (Gly), E designates glutamic acid (Glu), F designates phenylalanine (Phe), A designates alanine (Ala), V designates valine (Val), K designates lysine (Lys), M designates methionine (Met), and R designates arginine (Arg).

<Evaluation of Effect of Inhibiting Entry of Beta-Amyloid into Brain I>

The inhibition of entry of blood beta-amyloid 1-42 into the brain by the peptide of Example 1 was experimentally verified. Specifically, in order to evaluate the effect of the peptide of Example 1 on inhibiting the entry of beta-amyloid 1-42 into the brain, which is the cause of Alzheimer's disease, 1 mg of beta-amyloid 1-42 (American Peptide Company, Sunnyvale, Calif., USA) was added with 2 ml of hexafluoroisopropanol (HFIP), allowed to stand at room temperature for 3 days, and aliquoted at 100 μl each into tubes. After evaporation of hexafluoroisopropanol (HFIP) using a speed vacuum, 10 μl of an anhydrous DMSO (dimethyl sulfoxide) solution was placed in one of the aliquoted tubes, so as to realize sufficient dissolution, after which 400 μl of phosphate buffer saline (PBS) was added thereto, thus preparing a 25 μM beta-amyloid 1-42 solution.

ICR mice (The Jackson Laboratory, Bar Harbor, Me., USA) were divided into a normal group, a control group and two test groups. The respective test groups were intraperitoneally administered with the peptide of Example 1 in amounts of 2.5 mg/kg and 25 mg/kg, and the control group was treated in the same manner as in the test group, with the exception that an excipient (10% DMSO in saline, 10 ml/kg) was used in lieu of the peptide of Example 1. After 20 min, the control group and the test groups were intravenously (i.v.) injected through the tail vein with 400 μl of 25 μM beta-amyloid 1-42. Furthermore, the normal group was treated in the same manner as in the control group, with the exception that beta-amyloid 1-42 was not added. 10 min after the tail venous injection of beta-amyloid, about 50 μl of blood was collected from the infraorbital vein of each mouse using a sodium-heparinized capillary tube, after which the mouse was immediately subjected to euthanasia with carbon dioxide ($CO_2$) gas and then the right hemisphere of the mouse was extracted and stored in liquid nitrogen. All the collected blood samples were centrifuged at 13,000 rpm for 10 min. The supernatant was isolated, placed in the prepared tube, and diluted at 1/4000, followed by ELISA (Enzyme-Linked ImmunoSorbent Assay or Enzyme-Linked ImmunoSpecific Assay) of beta-amyloid 1-42.

The frozen right hemisphere was added with 3 ml of a RIPA buffer (Radio Immuno Precipitation Assay buffer), sonicated, and centrifuged, after which the supernatant was isolated, followed by protein concentration measurement through BCA assay (bicinchoninic acid assay). BCA assay was performed in accordance with the kit (Thermo Scientific, Waltham, Mass., USA, Cat. No. 23227) protocol. The beta-amyloid 1-42 concentration in the brain was measured through ELISA in a RIPA-homogenate. ELISA was performed in accordance with the kit (IBL International, Hamburg, Germany, Code No. 27711) protocol.

The results are shown in FIG. 1. FIG. 1 is graphs showing the results of evaluation of the effect of inhibiting the entry of blood beta-amyloid into the brain according to an embodiment of the present invention, the left graph of FIG. 1 illustrating the results of measurement of the beta-amyloid concentration in the brain in the normal group, control group and two test groups (a test group administered with 2.5 mg/kg of peptide and a test group administered with 25 mg/kg of peptide), and the right graph thereof illustrating the results of measurement of the blood (plasma) beta-amyloid concentration. As shown therein, the beta-amyloid 1-42 concentrations in the brain were measured to be 195.5±5.6 pg/mg and 187.8±2.4 pg/mg in the test group intraperitoneally administered with 2.5 mg/kg of peptide of Example 1 and the test group intraperitoneally administered with 25 mg/kg of peptide of Example 1, respectively, indicating that the beta-amyloid level in the brain was decreased in a concentration-dependent manner compared to the control group. These results were considered statistically significant ($p<0.01$). On the other hand, the plasma beta-amyloid levels were not greatly different in any of the control and test groups. Consequently, the entry of blood beta-amyloid 1-42 into the brain might be inhibited in a concentration-dependent manner by the peptide of Example 1.

Therefore, the peptide of the present invention is capable of inhibiting the entry of blood beta-amyloid 1-42 into the brain, thus making it possible to treat and/or prevent Alzheimer's disease, dementia such as vascular dementia, alcoholic dementia and dementia with Lewy bodies, Parkinson's disease, Huntington's disease, and/or inflammation of the brain.

Diseases caused by the deposition of beta-amyloid introduced into the brain are known to be Alzheimer's disease, dementia such as vascular dementia, alcoholic dementia and dementia with Lewy bodies, Parkinson's disease, Huntington's disease, inflammation of the brain, and the like (Irvine G B, El-Agnaf O M, Shankar G M, Walsh D M. Protein aggregation in the brain: the molecular basis for Alzheimer's and Parkinson's diseases. Mol Med. 2008; 14(7-8):451-64, etc.), and the peptide of the present invention is able to inhibit the entry of blood beta-amyloid 1-42 into the brain, thus enabling the treatment and/or prevention of such diseases.

<Evaluation of Learning and Memory Recovery Effects Using Animal Models>

The learning and memory recovery effects of the peptide of Example 1 were experimentally verified. Specifically, in order to evaluate the effect of the peptide of Example 1 on inhibiting learning and memory reduction, which are symptoms of Alzheimer's disease, 30-week-old double transgenic mouse (DTg mouse, Jackson Laboratory, USA) models having induced human Alzheimer's disease, obtained in a manner in which a human-derived gene of beta-amyloid precursor protein APP (APPsw; amyloid mutation) having Swedish mutation and a human-derived gene in the form of exon-9 deletion of a gamma secretase PSI gene were overexpressed in the brain through genetic manipulation, were used for tests.

DTg mice are known to show amyloid plaques in the brain about 1.5 months after birth, with cognitive dysfunctions shown from 4-5 months (Oakley H, Cole S L, Logan S, Maus E, Shao P, Craft J, Guillozet-Bongaarts A, Ohno M, Disterhoft J, Van Eldik L, Berry R, Vassar R. "Intraneuronal beta-amyloid aggregates, neurodegeneration, and neuron loss in transgenic mice with five familial Alzheimer's disease mutations: potential factors in amyloid plaque formation." J Neurosci. 2006 Oct. 4; 26(40):10129-40), and were used as animal models to determine whether the peptide of Example 1 exhibits learning and memory recovery effects.

The test animals were acclimated in an animal room after purchase in accordance with the Guidelines for Experimental Animal Tests and treated in accordance with the approved Animal Experimental Plan. The test conditions were maintained at a temperature of 23±1° C. and a humidity of 50±5%, and the light/dark cycle was 12 hr (07:00 lighting off-19:00 lighting on). During the testing, animals were free to consume water and feed. The test animals were divided into two groups of 10 animals each, one group being the control group and the other group being the test group. In the test group, the peptide of Example 1 was intraperitoneally administered at a dose of 50 mg/kg using a syringe once a day, 5 times a week, for a total of 13 weeks. The control group was treated in the same manner as in the test group, with the exception that an excipient (10% DMSO in saline, 10 ml/kg) was used in lieu of the peptide of Example 1. 10 weeks after the administration of the peptide of Example 1, a behavioral test (Y-maze test) was performed once.

The Y-maze test is an experiment to observe the voluntary tendency of an animal to search a new environment using short-term memory ability. The test was conducted by placing the animal in the center of a maze and allowing it to move freely in the maze for 8 min to thus visually observe and record the order in which the animal enters each branch. Spontaneous alternation (%) was calculated using the following equation.

$$\text{Spontaneous alternation (\%)}=\{(\text{actual alternation number})/(\text{total alternation number}-2)\}\times 100$$

The actual alternation number was incremented by one when the animal entered three different branches in succession without repeating a branch. Statistical processing of test results was performed using the SPSS program (IBM SPSS Statistics). Statistical significance was assayed for the control group versus the test group (administered with the peptide of Example 1) using an unpaired t-test. Significance was accepted at $p<0.05$ and $p<0.01$. The results are shown in FIG. 2.

Figure 2:
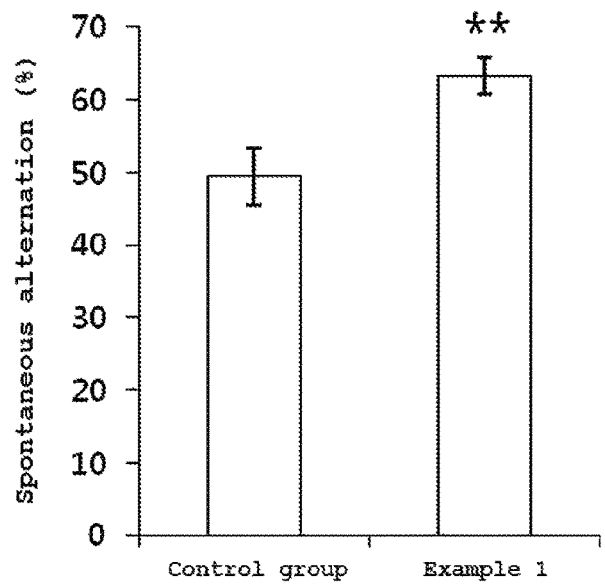
FIG. 2 is a graph showing the results of evaluation of the effect on animal learning and memory recovery according to an embodiment of the present invention.

FIG. 2 is a graph showing the results of evaluation of the effect on animal learning and memory recovery according to an embodiment of the present invention. As shown in FIG. 2, the spontaneous alternation values were measured to be 49.44±3.88% in the control group and 63.22±2.56% in the test group administered with the peptide of Example 1. In the test group administered with the peptide of Example 1, the learning and memory effects were recovered significantly ($P<0.01$).

Therefore, the peptide of Example 1 can be concluded to be effective at recovering learning and memory.

Consequently, the treatment and/or prevention of Alzheimer's disease, dementia such as vascular dementia, alcoholic dementia and dementia with Lewy bodies, Parkinson's disease, and the like which are treated and/or prevented through learning and memory recovery are deemed to be possible through learning and memory recovery by means of the peptide of the present invention.

<Evaluation of Effect of Changing Biomarker in Animal Models>

In order to evaluate the effect of changing the biomarker using animal models in which an administration period of a total of 13 weeks was terminated in the <Evaluation of learning and memory recovery effects using animal models> test, the following test was conducted. After termination of intraperitoneal administration for a total of 13 weeks, the animal models were subjected to euthanasia using carbon dioxide ($CO_2$) and the brain thereof was immediately extracted. Upon brain extraction, the entire brain was taken out so as not to be scratched, and was then lightly washed with saline solution. The brain hemispheres were separated from each other using a surgical scalpel, and the left hemisphere was placed in a prepared EP tube (EpPendorf tube), rapidly cooled in liquid nitrogen, and stored in a deep freezer at −80° C. until the next experiment.

The left hemisphere stored in a deep freezer at −80° C. was placed in a RIPA buffer (Radio Immuno Precipitation Assay buffer) and sonicated, thus preparing a brain homogenate. Thereafter, the amount of protein was measured through BCA assay (BicinChoninic Acid assay). BCA assay was performed in accordance with the kit (Thermo Scientific, saltham, MA, USA, Cat. No. 23227) protocol. The biomarker expression level was measured through ELISA, and ELISA assay was performed in accordance with the kit{Amyloid-beta(1-42) Elisa kit: IBL International, Hamburg, Germany (27711), TNF-alpha ELISA kit: Koma Biotech, Seoul, Korea (K0331186P), GFAP Elisa kit: Millipore Corporation, Billerica, Mass., USA (NS830)} protocol. After completion of all the reactions, the OD (Optical Density) value of the sample was measured at 450 nm using a spectrophotometer and the concentration was calculated using a quantitative analysis program.

The biomarkers measured through ELISA were beta-amyloid 1-42, TNF-alpha, and GFAP (glial fibrillary acidic protein). The biomarker expression level measured through ELISA was determined by calculating the mean value and standard deviation in each of the control group and the test group (a group administered with 50 mg/kg peptide of Example 1).

Figure 3:
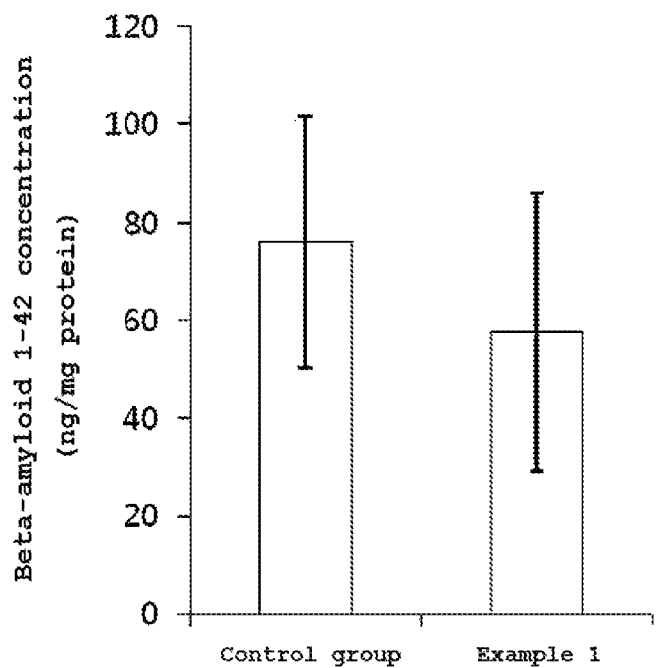
FIG. 3 is a graph showing the results of evaluation of the effect of reducing beta-amyloid 1-42 according to an embodiment of the present invention.
Figure 4:
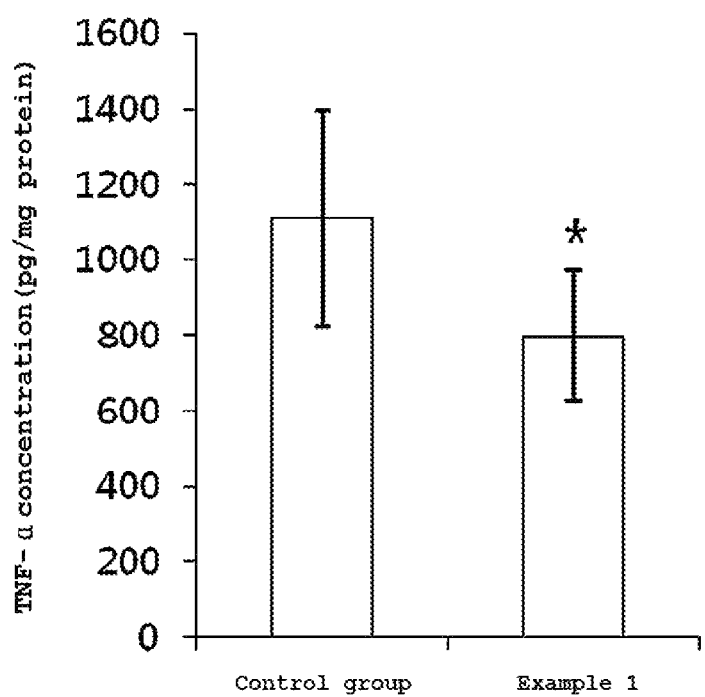
FIG. 4 is a graph showing the results of evaluation of the effect of reducing TNF-alpha according to an embodiment of the present invention.
Figure 5:
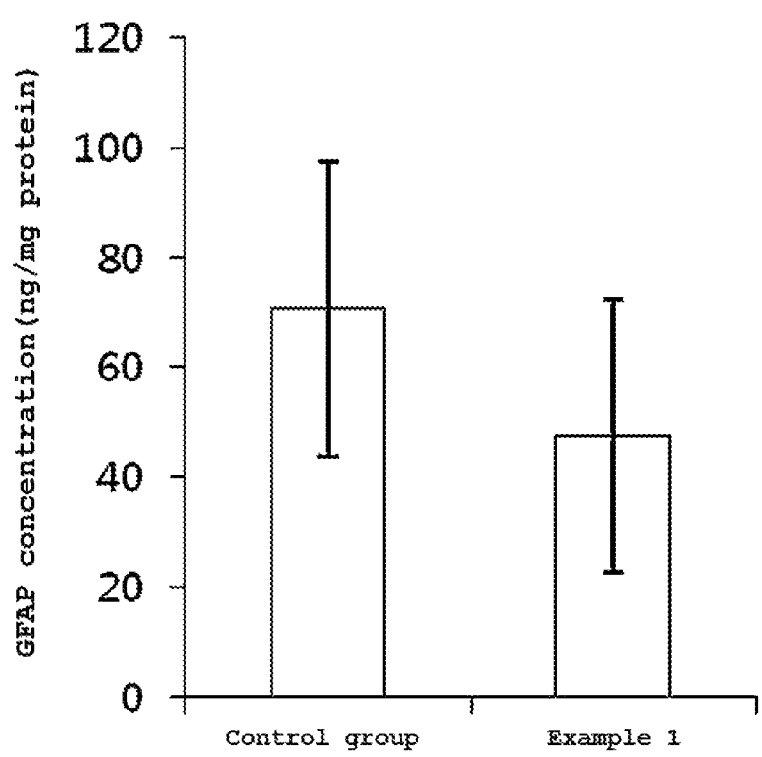
FIG. 5 is a graph showing the results of evaluation of the effect of reducing GFAP according to an embodiment of the present invention.

The results are shown in FIGS. 3 to 5.

FIG. 3 is a graph showing the results of evaluation of the effect of reducing beta-amyloid 1-42 according to an embodiment of the present invention. As shown in FIG. 3, the beta-amyloid 1-42 concentration of the control group was measured to be 76.03±25.63 ng/mg protein, and the beta-amyloid 1-42 concentration of the test group was measured to be 57.56±28.47 ng/mg protein, which was slightly decreased compared to the control group.

FIG. 4 is a graph showing the results of evaluation of the effect of reducing TNF-alpha according to an embodiment of the present invention. As shown in FIG. 4, the TNF-alpha concentration of the control group was measured to be 1109.91±285.30 pg/mg protein, and the TNF-alpha concentration of the test group was measured to be 798.99±172.90 pg/mg protein, which was decreased statistically significantly ($p<0.05$) compared to the control group. TNF-alpha is an inflammatory factor, the reduction of which may be interpreted to mean the inhibition of inflammation. Based on these results, the peptide of Example 1 can be concluded to inhibit inflammation of the brain.

FIG. 5 is a graph showing the results of evaluation of the effect of reducing GFAP according to an embodiment of the present invention. As shown in FIG. 5, in the astrocyte marker GFAP (glial fibrillary acidic protein), the GFAP concentration of the control group was measured to be 70.61±26.82 ng/mg protein, and the GFAP concentration of the test group was measured to be 47.63±24.92 ng/mg protein, which was slightly reduced compared to the control group.

Based on the biomarker test results, upon the long-term administration of the peptide of Example 1, it can be confirmed that the beta-amyloid level in the brain is reduced and that the inflammatory response is suppressed. This change in biomarker is also deemed to support the results of improvement of the learning and memory recovery in animals using the peptide of Example 1.

Based on the above results, the peptide or pharmaceutically acceptable salt thereof according to the present invention is capable of treating and/or preventing Alzheimer's disease, dementia such as vascular dementia, alcoholic dementia and dementia with Lewy bodies, Parkinson's disease, Huntington's disease, and/or inflammation of the brain, and the treatment and/or prevention thereof can be found to be due to the inhibition of entry of beta-amyloid into the brain, inhibition of deposition of beta-amyloid in the brain and/or inhibition of inflammation of the brain.

<Evaluation of Effect of Inhibiting Entry of Beta-Amyloid into Brain II>

Based on the test results of Example 1, the following test was conducted in order to evaluate whether Example 2 and Comparative Examples 1 and 2, in addition to Example 1, are effective at inhibiting the entry of beta-amyloid 1-42 into the brain.

The peptide of Example 2 is a peptide (DGEF) consisting of four amino acids obtained by excluding terminal F from the peptide of Example 1, the peptide of Comparative Example 1 is a peptide consisting of the key amino acid sequence (DAEF) among neuroprotective peptides disclosed in International Publication No. WO 2006/031330 A2, and the peptide of Comparative Example 2 is a peptide having the greatest effect among neuroprotective peptides known to comprise the corresponding amino acid sequence.

Specifically, 1 mg of beta-amyloid 1-42 (American Peptide Company, Sunnyvale, Calif., USA) was added with 2 ml of hexafluoroisopropanol (HFIP), allowed to stand at room temperature for 3 days, and aliquoted at 100 µl each into tubes. After evaporation of hexafluoroisopropanol (HFIP) using a speed vacuum, 10 µl of an anhydrous DMSO (dimethyl sulfoxide) solution was placed in one of the aliquoted tubes, so as to realize sufficient dissolution, after which 400 µl of phosphate buffer saline (PBS) was added thereto, thus preparing a 25 µM beta-amyloid 1-42 solution.

ICR mice (The Jackson Laboratory, Bar Harbor, Me., USA) were divided into a normal group, a control group and four test groups. The respective test groups were intraperitoneally administered with the peptide of each of Example 1, Example 2, Comparative Example 1, and Comparative Example 2 in amounts of 25 mg/kg, and the control group was treated in the same manner as in the test group, with the exception that an excipient (10% DMSO in saline, 10 ml/kg) was used in lieu of the peptide. After 20 min, the control group and the test groups were intravenously (i.v.) injected through the tail vein with 400 µl of 25 µM beta-amyloid 1-42. Furthermore, the normal group was treated in the same manner as in the control group, with the exception that beta-amyloid 1-42 was not added. 10 min after the tail venous injection of beta-amyloid, about 50 µl of blood was collected from the infraorbital vein of each mouse using a sodium-heparinized capillary tube, after which the mouse was immediately subjected to euthanasia with carbon dioxide ($CO_2$) gas and then the right hemisphere of the mouse was extracted and stored in liquid nitrogen. All the collected blood samples were centrifuged at 13,000 rpm for 10 min. The supernatant was isolated, placed in the prepared tube, and diluted at 1/4000, followed by ELISA (Enzyme-Linked ImmunoSorbent Assay or Enzyme-Linked ImmunoSpecific Assay) of beta-amyloid 1-42.

The frozen right hemisphere was added with 3 ml of a RIPA buffer (Radio Immuno Precipitation Assay buffer), sonicated, and centrifuged, after which the supernatant was isolated, followed by protein concentration measurement through BCA assay (bicinchoninic acid assay). BCA assay was performed in accordance with the kit (Thermo Scientific, Waltham, Mass., USA, Cat. No. 23227) protocol. The beta-amyloid 1-42 concentration in the brain was measured through ELISA in a RIPA-homogenate. ELISA was performed in accordance with the kit (IBL International, Hamburg, Germany, Code No. 27711) protocol.

The results are shown in Table 2 below.

TABLE 2

| | Beta-amyloid 1-42 concentration in brain (pg/mg protein) |
|---|---|
| Normal group | 0.0 ± 11.9 |
| Control group | 60.8 ± 14.8 |
| Example 1 treatment group | 54.8 ± 8.0 |
| Example 2 treatment group | 48.8 ± 14.7 |
| Comparative Example 1 treatment group | 69.5 ± 6.1 |
| Comparative Example 2 treatment group | 87.6 ± 14.9 |

As is apparent from Table 2, the peptide of Example 2 effectively inhibited the entry of beta-amyloid into the brain, like the peptide of Example 1. As the peptide of Example 1, the peptide of Example 2 was able to inhibit the entry of beta-amyloid into the brain to thus suppress the deposition of beta-amyloid in the brain. Consequently, the peptide of Example 2 is also deemed to enable the treatment and/or prevention of Alzheimer's disease, dementia such as vascular dementia, alcoholic dementia and dementia with Lewy bodies, Parkinson's disease, Huntington's disease, and/or inflammation of the brain, associated with the deposition of beta-amyloid in the brain, and such treatment and/or prevention can be found to be due to inhibition of entry of beta-amyloid into the brain, inhibition of deposition of beta-amyloid in the brain and/or inhibition of inflammation of the brain.

However, the peptides of Comparative Examples 1 and 2 did not inhibit the entry of beta-amyloid into the brain, unlike the peptide of Example 1.

Accordingly, the peptide or pharmaceutically acceptable salt thereof according to the present invention can be concluded to exhibit effects quite different from those of known neuroprotective peptides.

Consequently, the present invention can be easily applied because the intracerebral action of beta-amyloid can be inhibited even without additional means for passing through a blood-brain barrier.

Moreover, the present invention is capable of inhibiting the intracerebral action of beta-amyloid fundamentally, and can be more directly applied in association with inhibition of the intracerebral action of beta-amyloid, and thus exhibits high applicability.

<Evaluation of Effect of Inhibiting Entry of Beta-Amyloid into Brain III>

The binding of the peptides of Examples 1 and 2 to RAGE was evaluated through the following test, whereby the entry of beta-amyloid into the brain was confirmed to be inhibited through suppression of the binding of beta-amyloid to RAGE.

This is based on the fact that RAGE (Receptor for Advanced Glycation End products), which is expressed on the endothelial cell membrane of the blood-brain barrier, plays a role in transporting beta-amyloid to the brain, and also on the fact that inhibitors for inhibiting the binding of RAGE and beta-amyloid have therapeutic or preventive effects on Alzheimer's disease, cognitive disorder, or dementia, associated with the deposition of beta-amyloid protein in the brain tissues (Neurology. 2004 Jun. 8; 62(11): 1984-1989; J Clin Invest. 2012 April; 122(4):1377-1392 etc.).

Specifically, the binding capacity of the peptide of Example 1 or 2 to RAGE was measured using MST (Microscale Thermophoresis).

Using a kit {Monolith NT™ Protein Labeling Kit RED-NHS (L001, NanoTemper Technologies)}, an extracellular domain recombinant protein RAGE (11629-H08H, Sino Biological Inc.) was bound to a RED fluorescent dye NT-647-NHS and then purified. Thereafter, a RAGE solution in which the concentration of the RED fluorescent dye NT-647-NHS labeled RAGE in an MST buffer (50 mM Tris-HCl pH 7.4, 150 mM NaCl, 10 mM $MgCl_2$, 0.05% Tween-20) solution was 20 μM was prepared. Also, a peptide solution was prepared in a 16-step dilution series, in which dilution was repeated with the MST buffer until the concentration of the peptide of Example 1 or Example 2 became 1.52 nM starting from 50 μM. Thereafter, the RAGE solution and the peptide solution were mixed in amounts of 100 μl each, injected into a capillary tube and then placed in the order of concentration in a Monolith NT. 115 tray (G009, NanoTemper technologies). The software was operated in accordance with the Monolith NT. 115 operating method. The same procedure was repeated three times, and the mean value of Kd (dissociation constant) was obtained.

Consequently, the Kd between the RAGE and the peptide of Example 1 was 76.86 nM and the Kd between the RAGE and the peptide of Example 2 was 80.89 nM, indicating that both of the peptides of Examples 1 and 2 were coupled with RAGE to thus suppress the binding of beta-amyloid and RAGE, thereby inhibiting the entry of beta-amyloid into the brain.

In conclusion, the peptide of the present invention is capable of suppressing the binding of RAGE and beta-amyloid, thus inhibiting the entry of beta-amyloid into the brain, whereby the intracerebral action of beta-amyloid can be prevented fundamentally. Therefore, the peptide or pharmaceutically acceptable salt thereof according to the present invention is deemed to enable the treatment and/or prevention of Alzheimer's disease, dementia such as vascular dementia, alcoholic dementia and dementia with Lewy bodies, Parkinson's disease, Huntington's disease, and/or inflammation of the brain, associated with the deposition of beta-amyloid in the brain. Moreover, the present invention can be more directly and easily applied in association with inhibition of the intracerebral action of beta-amyloid, and thus exhibits high applicability.

<Preparation Example> Preparation of a Dosage Form for Injection 500 mg of a peptide prepared in the same manner as in Example 1 or 2 was dissolved in saline solution to make 10 ml of a solution. This solution was charged in an ampoule for an injection, yielding a dosage form for injection of Preparation Example 1 or 2.

INDUSTRIAL APPLICABILITY

The present invention is effective at inhibiting the entry of beta-amyloid into the brain. Also, the present invention can be more easily applied in association with inhibition of the intracerebral action of beta-amyloid, thus exhibiting high applicability. Therefore, the present invention is industrially applicable.

The invention claimed is:

1. A peptide consisting of the amino acid sequence of SEQ ID NO: 1 or a pharmaceutically acceptable salt thereof.

2. An inhibitor for inhibiting entry of beta-amyloid into a brain, comprising the peptide or the pharmaceutically acceptable salt thereof of claim 1.

3. A pharmaceutical composition for treatment of at least one disease selected from among Alzheimer's disease, dementia, Parkinson's disease, Huntington's disease, and inflammation of a brain, the pharmaceutical composition comprising the peptide or the pharmaceutically acceptable salt thereof of claim 1.

4. The pharmaceutical composition of claim 3, wherein the at least one disease selected from among Alzheimer's disease, dementia, Parkinson's disease, Huntington's disease, and inflammation of the brain is caused by deposition of beta-amyloid in the brain.

5. The pharmaceutical composition of claim 3, wherein the treatment is due to inhibition of entry of beta-amyloid into the brain.

* * * * *

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial Sequence
<220> FEATURE:
<223> OTHER INFORMATION: peptide

<400> SEQUENCE: 1

Asp Gly Glu Phe Phe
1               5

<210> SEQ ID NO 2
<211> LENGTH: 4
<212> TYPE: PRT
<213> ORGANISM: Artificial Sequence
<220> FEATURE:
<223> OTHER INFORMATION: peptide

<400> SEQUENCE: 2

Asp Gly Glu Phe
1

<210> SEQ ID NO 3
<211> LENGTH: 4
<212> TYPE: PRT
<213> ORGANISM: Artificial Sequence
<220> FEATURE:
<223> OTHER INFORMATION: peptide

<400> SEQUENCE: 3

Asp Ala Glu Phe
1

<210> SEQ ID NO 4
<211> LENGTH: 8
<212> TYPE: PRT
<213> ORGANISM: Artificial Sequence
<220> FEATURE:
<223> OTHER INFORMATION: peptide

<400> SEQUENCE: 4

Val Lys Met Asp Ala Glu Phe Arg
1               5
```